United States Patent
Claas et al.

(10) Patent No.: US 9,186,304 B2
(45) Date of Patent: Nov. 17, 2015

(54) PEG-FREE ANTIPERSPIRANT OIL-IN-WATER EMULSIONS HAVING IMPROVED FEEL

(71) Applicant: Henkel AG & Co. KGaA, Duesseldorf (DE)

(72) Inventors: Marcus Claas, Hilden (DE); Bernhard Banowski, Duesseldorf (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 14/309,997

(22) Filed: Jun. 20, 2014

(65) Prior Publication Data

US 2014/0301963 A1    Oct. 9, 2014

Related U.S. Application Data

(63) Continuation of application No. PCT/EP2012/074251, filed on Dec. 3, 2012.

(30) Foreign Application Priority Data

Dec. 21, 2011 (DE) .......................... 10 2011 089 340

(51) Int. Cl.
| | |
|---|---|
| *A61K 8/26* | (2006.01) |
| *A61K 8/06* | (2006.01) |
| *A61Q 15/00* | (2006.01) |
| *A61K 8/34* | (2006.01) |
| *A61K 8/37* | (2006.01) |
| *A61K 8/39* | (2006.01) |
| *A61K 8/44* | (2006.01) |
| *A61K 8/73* | (2006.01) |
| *A61K 8/362* | (2006.01) |
| *A61K 8/42* | (2006.01) |

(52) U.S. Cl.
CPC . *A61K 8/062* (2013.01); *A61K 8/26* (2013.01); *A61K 8/347* (2013.01); *A61K 8/362* (2013.01); *A61K 8/375* (2013.01); *A61K 8/39* (2013.01); *A61K 8/42* (2013.01); *A61K 8/442* (2013.01); *A61K 8/731* (2013.01); *A61Q 15/00* (2013.01)

(58) Field of Classification Search
CPC ................................ A61Q 15/00; A61K 8/26
See application file for complete search history.

(56) References Cited

U.S. PATENT DOCUMENTS

| | | | |
|---|---|---|---|
| 2,571,030 | A | 10/1951 | Govett et al. |
| 3,887,692 | A | 6/1975 | Gilman |
| 3,904,741 | A | 9/1975 | Jones et al. |
| 4,017,599 | A | 4/1977 | Rubino |
| 4,359,456 | A | 11/1982 | Gosling et al. |
| 4,775,528 | A | 10/1988 | Callaghan et al. |
| 5,643,559 | A | 7/1997 | Eigen et al. |
| 5,676,937 | A | 10/1997 | Eigen et al. |
| 6,010,688 | A | 1/2000 | Shen |
| 7,294,330 | B2 | 11/2007 | Banowski et al. |
| 2005/0203179 | A1 | 9/2005 | Banowski et al. |
| 2011/0274637 | A1 | 11/2011 | Milardovic et al. |

FOREIGN PATENT DOCUMENTS

| | | |
|---|---|---|
| DE | 3018132 A1 | 11/1981 |
| DE | 102010000746 A1 | 1/2011 |
| EP | 0650720 A1 | 5/1995 |
| EP | 0495918 B1 | 1/1996 |
| EP | 1428519 A2 | 6/2004 |
| EP | 1428520 A2 | 6/2004 |
| EP | 1430879 A2 | 6/2004 |
| GB | 1347950 | 2/1974 |
| GB | 2048229 A | 12/1980 |
| GB | 2335596 A | 9/1999 |
| WO | 01/99376 A2 | 12/2001 |
| WO | 2006/079934 A2 | 8/2006 |
| WO | 2010/031657 A2 | 3/2010 |
| WO | 2010/046291 A2 | 4/2010 |

OTHER PUBLICATIONS

PCT International Search Report (PCT/EP2012/074251) dated Oct. 20, 2014.
"Further Surfactant Launches from In-Cosmetics 2010", Focus on Surfactants, Elsevier Engineering Information Inc., vol. 2010, Issue 7, pp. 2-3, Jul. 2010, XP027119143.

*Primary Examiner* — Carlos Azpuru
(74) *Attorney, Agent, or Firm* — P. Scott Smith

(57) ABSTRACT

An antiperspirant composition in the form of an oil-in-water emulsion includes a PEG-free emulsifier system including selected polyglycerol citrate esters and an N-acylglutamate.

4 Claims, No Drawings

PEG-FREE ANTIPERSPIRANT OIL-IN-WATER EMULSIONS HAVING IMPROVED FEEL

FIELD OF THE INVENTION

The present invention generally relates to perspiration-inhibiting compositions in the form of a lotion-like oil-in-water emulsion having a polyethylene oxide-free emulsifier system, which are suitable in particular for application with a roll-on applicator and exhibit good shelf stability and a non-greasy skin feel.

BACKGROUND OF THE INVENTION

There are numerous possibilities for applying cosmetic compositions onto the skin for skin care and body care. Creams, salves, and lotions are usually taken out of a jar, a tube, or a pump dispenser and applied and rubbed on by hand. Dimensionally stable stick compounds are wiped over the skin out of a stick dispenser until an effective quantity is applied. Gels and creams can also be applied using stick-like dispensers that are wiped over the skin with a dispenser surface. Numerous different application forms have been developed in particular for perspiration-inhibiting and/or deodorizing compositions for the armpit region; besides those already recited, these are chiefly the sprays that include and are free of greenhouse gases, and roll-on compositions. In the case of the latter, a slightly thickened liquid is applied from a reservoir container via a rotatably mounted ball, by rolling it over the skin. Numerous cosmetic active agents, among them the perspiration-inhibiting aluminum salts, are water soluble, and release thereof on the skin could be delayed by oil and fat constituents of the cosmetic. As an entirely aqueous product, however, the product would be almost impossible to dispense and thus would be unacceptable to the consumer. Slight thickening, however, allows such a composition to be used conveniently with a roll-on applicator. Polymeric thickening agents are often employed. A disadvantage here is that in the required concentrations, most polymeric thickening agents generate a very sticky skin feel. In addition, many of these thickeners have no additional cosmetic care-providing effects. Emulsions having a low oil and fat content represent an advantageous alternative to this. Emulsion formation already results in a rise in viscosity even without polymer thickeners, or with only small quantities thereof. The oil and fat portion of the emulsion furthermore provides a skin-care-providing effect.

Unlike microemulsions, emulsions are thermodynamically unstable. The thermodynamically stable microemulsions can usually be stabilized only by a relatively high emulsifier agent concentration. A high concentration of emulsifier agents, however, can in the least favorable case have a skin-irritating effect and is therefore avoided if at all possible. In addition, microemulsions often form only in a very narrow mixing range of the individual components. For cosmetic compositions having multiple constituents, it can therefore sometimes be very difficult in terms of development engineering to establish suitable microemulsion ranges. Emulsions are stable for a certain time because coalescence of the dispersed droplets is kinetically inhibited. This kinetic inhibition can be overcome by storage at high temperatures (relevant in particular for production and marketing in hot countries), or when stored in a context of large temperature fluctuations (e.g. in insufficiently climate-controlled sales areas, when transported over long distances). The high salt concentration in antiperspirant compositions, due to the relatively high concentration of perspiration-inhibiting active agents, can also promote emulsion destabilization (e.g. due to salting-out effects).

Typical antiperspirant roll-on emulsions are stabilized with polyethylene-glycol-including emulsifier agents, in particular with combinations of an emulsifier agent having a low HLB value, such as Steareth-2, and an emulsifier agent having a high HLB value, such as Steareth-20 or Steareth-21. The majority of the deodorant or antiperspirant roll-on formulations on the market having aluminum salts (aluminum chlorohydrates; aluminum zirconium chlorohydrates) in the form of oil-in-water emulsions include ethoxylated (=polyethylene-glycol-containing, PEG-containing) fatty alcohols or fatty acids as emulsifier agents, and propoxylated (=polypropylene-glycol-containing, PPG-containing) oils (usually ethers) as co-emulsifiers. As in other cosmetic sectors, opportunities for replacing EO/PO adducts (EO=ethylene oxide, PO=propylene oxide) are being sought in the deodorant and antiperspirant sector as well.

BRIEF SUMMARY OF THE INVENTION

It has been found, surprisingly, that by using at least one surface-active compound having an HLB value in the range from 9 to 15, selected from partial esters of a polyglycerol that comprises 3, 4, or 5 glycerol units with a linear saturated alkanoic acid having 8 to 22 carbon atoms and with an organic edible acid, in combination with at least one N-acyl-L-glutamic acid sodium salt, furthermore at least one structuring agent selected from linear saturated 1-alkanols having 14 to 22 carbon atoms and glyceryl mono- and diesters of linear or branched, saturated or unsaturated carboxylic acids having 8 to 22 carbon atoms, and further a relatively low oil proportion, it is possible to produce stable oil-in-water emulsions that exhibit a high tolerance with respect to aluminum salts and the low pH values, in the range from 4 to 5, associated therewith. Various polar or nonpolar oils that are liquid at room temperature can be employed as an oil component. The selection criterion for the oil here can be, for example, the ability to be washed out of textiles. The viscosity necessary for convenient application by means of a roll-on applicator can be established by means of various hydrogel formers, in particular by means of a biopolymer.

The novel antiperspirant emulsions are free of EO adducts or PO adducts and exhibit improved haptics, in particular less stickiness. In set-off tests on dark textiles in the armpit, the novel antiperspirant emulsions exhibit residua less than or the same as conventional roll-on emulsions based on Steareth-2/Steareth-21.

A perspiration-inhibiting composition in the form of an oil-in-water emulsion that is not a microemulsion includes a) at least one perspiration-inhibiting aluminum salt in a total quantity from 2 to 40 wt %, preferably 8 to 35 wt %, particularly preferably 10 to 28 wt %, and extraordinarily preferably 12 to 20 wt %, wherein the "wt %" indications refer to the total weight of active substance (USP), free of water of crystallization and free of ligands, in the agent; and in addition thereto b) in a total quantity from 0.1 to 2 wt %, preferably 0.3 to 1.5 wt %, particularly preferably 0.5 to 1.1 wt %, extraordinarily preferably 0.6 to 0.8 wt %, at least one surface-active compound having an HLB value in the range from 9 to 15, selected from the partial esters of a polyglycerol that comprises 3, 4, or 5 glycerol units with a linear or branched, saturated or unsaturated carboxylic acid having 8 to 22 carbon atoms and with an organic edible acid; and in addition thereto c) in a total quantity from 0.1 to 2.0 wt %, preferably 0.3 to 1.2 wt %, particularly preferably 0.6 to 1.1 wt %, extraordinarily preferably 0.8 to 1.0 wt %, at least one N-acyl-L-glutamic acid sodium salt of formula (GLUT-1)

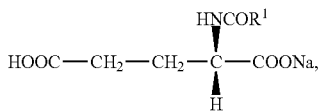

(GLUT-1)

in which $R^1CO$ represents a linear or branched, saturated or unsaturated acyl group having 6 to 22 carbon atoms, preferably having 8 to 18 carbon atoms; and in addition thereto d) at least one cosmetic oil, liquid under standard conditions, that is not a fragrance and not an essential oil, in a total quantity from 0.5 to 10 wt %, preferably 1 to 8 wt %, particularly preferably 1.5 to 6 wt %, extraordinarily preferably 2 to 4.5 wt %; and in addition thereto e) at least one hydrogel-forming polymer in a total quantity from 0.08 to 1 wt %, preferably 0.1 to 0.8 wt %, particularly preferably 0.15 to 0.6 wt %, extraordinarily preferably 0.2 to 0.4 wt %; and in addition thereto f) in a total quantity from 0.05 to 4 wt %, preferably 0.5 to 3.5 wt %, particularly preferably 1 to 3 wt %, and extraordinarily preferably 1.5 to 2.5 wt %, at least one structuring agent selected from linear saturated 1-alkanols having 14 to 22 carbon atoms, glyceryl mono- and diesters of linear or branched, saturated or unsaturated carboxylic acids having 8 to 22 carbon atoms, linear saturated 1-alkanecarboxylic acids having 14 to 22 carbon atoms, mono- and diesters of ethylene glycol with linear saturated and unsaturated fatty acids having 12 to 30, in particular 14 to 22 carbon atoms, the mono-, di-, tri-, and tetraesters of pentaerythritol with linear saturated and unsaturated fatty acids having 12 to 30, in particular 14 to 22 carbon atoms, as well as mixtures of said structuring agents; and in addition thereto g) water in a total quantity from 30 to 90 wt %, preferably 40 to 80 wt %, particularly preferably 60 to 78 wt %, extraordinarily preferably 65 to 73 wt %, wherein the "wt %" indications refer in each case to the total weight of the composition.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject of the present Application is therefore perspiration-inhibiting compositions in the form of an oil-in-water emulsion that are not a microemulsion, including
a) at least one perspiration-inhibiting aluminum salt in a total quantity from 2 to 40 wt %, preferably 8 to 35 wt %, particularly preferably 10 to 28 wt %, and extraordinarily preferably 12 to 20 wt %, wherein the "wt %" indications refer to the total weight of active substance (USP), free of water of crystallization and free of ligands, in the agent,
and in addition thereto
b) in a total quantity from 0.1 to 2 wt %, preferably 0.3 to 1.5 wt %, particularly preferably 0.5 to 1.1 wt %, extraordinarily preferably 0.6 to 0.8 wt %, at least one surface-active compound having an HLB value in the range from 9 to 15, selected from the partial esters of a polyglycerol that comprises 3, 4, or 5 glycerol units with a linear or branched, saturated or unsaturated carboxylic acid having 8 to 22 carbon atoms and with an organic edible acid, and in addition thereto
c) in a total quantity from 0.1 to 2.0 wt %, preferably 0.3 to 1.2 wt %, particularly preferably 0.6 to 1.1 wt %, extraordinarily preferably 0.8 to 1.0 wt %, at least one N-acyl-L-glutamic acid sodium salt of formula (GLUT-1)

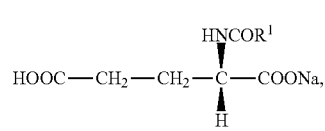

(GLUT-1)

in which $R^1CO$ represents a linear or branched, saturated or unsaturated acyl group having 6 to 22 carbon atoms, preferably having 8 to 18 carbon atoms,
and in addition thereto
d) at least one cosmetic oil, liquid under standard conditions, that is not a fragrance and not an essential oil, in a total quantity from 0.5 to 10 wt %, preferably 1 to 8 wt %, particularly preferably 1.5 to 6 wt %, extraordinarily preferably 2 to 4.5 wt %,
and in addition thereto
e) at least one hydrogel-forming polymer in a total quantity from 0.08 to 1 wt %, preferably 0.1 to 0.8 wt %, particularly preferably 0.15 to 0.6 wt %, extraordinarily preferably 0.2 to 0.4 wt %,
and in addition thereto
f) in a total quantity from 0.05 to 4 wt %, preferably 0.5 to 3.5 wt %, particularly preferably 1 to 3 wt %, and extraordinarily preferably 1.5 to 2.5 wt %, at least one structuring agent selected from linear saturated 1-alkanols having 14 to 22 carbon atoms, glyceryl mono- and diesters of linear or branched, saturated or unsaturated carboxylic acids having 8 to 22 carbon atoms, linear saturated 1-alkanecarboxylic acids having 14 to 22 carbon atoms, mono- and diesters of ethylene glycol with linear saturated and unsaturated fatty acids having 12 to 30, in particular 14 to 22 carbon atoms, the mono-, di-, tri-, and tetraesters of pentaerythritol with linear saturated and unsaturated fatty acids having 12 to 30, in particular 14 to 22 carbon atoms, as well as mixtures of said structuring agents,
and in addition thereto
g) water in a total quantity from 30 to 90 wt %, preferably 40 to 80 wt %, particularly preferably 60 to 78 wt %, extraordinarily preferably 65 to 73 wt %,
wherein the "wt %" indications refer in each case to the total weight of the composition.

Preferred compositions according to the present invention include polyethylene-glycol-containing and polypropylene-glycol-containing compounds in a total quantity from 0 to a maximum of 0.3 wt %, preferably from 0 to a maximum of 0.2 wt %, particularly preferably from 0 to a maximum of 0.1 wt %, based in each case on the total weight of the composition.

Antiperspirant active agents.

The compositions according to the present invention include as an antiperspirant active agent at least one perspiration-inhibiting aluminum salt in a total quantity from 2 to 40 wt %, preferably 8 to 35 wt %, particularly preferably 10 to 28 wt %, and extraordinarily preferably 12 to 20 wt %, wherein the "wt %" indications refer to the total weight of active substance (USP), free of water of crystallization and free of ligands, in the composition.

The perspiration-inhibiting aluminum salts are preferably selected from water-soluble astringent inorganic and organic salts of aluminum and of aluminum-zirconium mixtures. Aluminosilicates and zeolites are not included according to the present invention among the antiperspirant active agents. "Water solubility" is understood according to the present invention as a solubility of at least 3 wt % at 20° C., i.e. that quantities of at least 3 g of the antiperspirant active agent are soluble in 97 g water at 20° C.

Particularly preferred antiperspirant active agents are selected from aluminum chlorohydrate, in particular aluminum chlorohydrate having the general formula $[Al_2(OH)_5Cl.1\text{-}6H_2O]_n$, preferably $[Al_2(OH)_5Cl.2\text{-}3H_2O]_n$, which can be present in nonactivated or in activated (depolymerized) form, as well as aluminum chlorohydrate having the general formula $[Al_2(OH)_4Cl_2.1\text{-}6H_2O]_n$, preferably $[Al_2(OH)_4Cl_2.2\text{-}3H_2O]_n$, which can be present in nonactivated or in activated (depolymerized) form.

The manufacture of preferred antiperspirant active agents is disclosed, for example, in U.S. Pat. No. 3,887,692, U.S. Pat. No. 3,904,741, U.S. Pat. No. 4,359,456, GB 2048229, and GB 1347950.

Also preferred are aluminum sesquichlorohydrate, aluminum dichlorohydrate, aluminum chlorohydrex propylene glycol (PG), aluminum or aluminum zirconium glycol complexes, e.g. aluminum or aluminum zirconium propylene glycol complexes, aluminum sesquichlorohydrex PG, aluminum PG dichlorohydrex, aluminum hydroxide, furthermore selected from aluminum zirconium chlorohydrates, such as aluminum zirconium trichlorohydrate, aluminum zirconium tetrachlorohydrate, aluminum zirconium pentachlorohydrate, aluminum zirconium octachlorohydrate, aluminum zirconium chlorohydrate/glycine complexes, such as aluminum zirconium trichlorohydrex glycine, aluminum zirconium tetrachlorohydrex glycine, aluminum zirconium pentachlorohydrex glycine, aluminum zirconium octachlorohydrex glycine, potassium aluminum sulfate $(KARSO_4)_2.12\ H_2O$, alum), aluminum undecylenoyl collagen amino acid, sodium aluminum lactate+aluminum sulfate, sodium aluminum chlorohydroxylactate, aluminum bromohydrate, aluminum chloride, aluminum salts of lipoamino acids, aluminum sulfate, aluminum lactate, aluminum chlorohydroxyallantoinate, and sodium aluminum chlorohydroxylactate.

Antiperspirant active agents particularly preferred according to the present invention are selected from so-called "activated" aluminum and aluminum-zirconium salts, which are also referred to as "enhanced activity" antiperspirant active agents. Such active agents are known in the existing art and also commercially obtainable. Their manufacture is disclosed, for example, in GB 2048229, U.S. Pat. No. 4,775,528, and U.S. Pat. No. 6,010,688.

Further preferred perspiration-inhibiting active agents are basic calcium-aluminum salts such as those disclosed e.g. in U.S. Pat. No. 2,571,030. These salts are manufactured by reacting calcium carbonate with aluminum chlorohydroxide or aluminum chloride and aluminum powder, or by adding calcium chloride dihydrate to aluminum chlorohydroxide.

Further preferred perspiration-inhibiting active agents are aluminum-zirconium complexes such as those disclosed, for example, in U.S. Pat. No. 4,017,599, which are buffered with salts of amino acids, in particular with alkali glycinates and alkaline-earth glycinates.

Water-soluble calcium salts preferred for stabilization of the perspiration-inhibiting salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

Amino acids preferred for stabilization of the perspiration-inhibiting salts are selected from glycine, alanine, leucine, isoleucine, β-alanine, valine, cysteine, serine, tryptophan, phenylalanine, methionine, β-amino-n-butanoic acid, and γ-amino-n-butanoic acid and salts thereof, in each case in the d-form, the l-form, and the dl-glycine is particularly preferred.

Hydroxyalkanoic acids preferred for stabilization of the perspiration-inhibiting salts are selected from glycolic acid and lactic acid.

Preferred perspiration-inhibiting aluminum zirconium salts have a molar metal-to-chloride ratio from 0.9 to 1.5, preferably from 0.9 to 1.3, particularly preferably from 0.9 to 1.1.

Zirconium-free aluminum salts particularly preferred according to the present invention have a molar metal-to-chloride ratio from 1.9 to 2.1. Zirconium-free aluminum sesquichlorohydrates particularly preferred according to the present invention have a molar metal-to-chloride ratio from 1.5:1 to 1.8:1.

Preferred aluminum zirconium chlorohydrates generally have the empirical formula $Al_nZr(OH)_{[3n+4-m(n+1)]}(Cl)_{[m(n+1)]}$, where n=2.0 to 10.0, preferably 3.0 to 8.0, m=0.77 to 1.11 (corresponding to a molar ratio of metal (Al+Zr) to chloride from 1.3 to 0.9), preferably m=0.91 to 1.11 (corresponding to M:Cl=1.1 to 0.9), and particularly preferably m=1.00 to 1.11 (corresponding to M:Cl=1.0 to 0.9), also very preferably m=1.02 to 1.11 (corresponding to M:Cl=0.98 to 0.9) and very preferably m=1.04 to 1.11 (corresponding to M:Cl=0.96 to 0.9). Some water of hydration is generally associatively bound in these salts, typically 1 to 6 mol water per mol salt, corresponding 1 to 16 wt %, preferably 4 to 13 wt % water of hydration.

Preferred aluminum zirconium chlorohydrates are usually associated with an amino acid in order to prevent polymerization of the zirconium species during manufacture. Preferred stabilizing amino acids are selected from glycine, alanine, leucine, isoleucine, β-alanine, cysteine, valine, serine, tryptophan, phenylalanine, methionine, β-amino-n-butanoic acid, and γ-amino-n-butanoic acid, and salts thereof, respectively in the d-form, l-form, and dl-form; glycine is particularly preferred. The amino acid is included in the salt in a quantity from 1 to 3 mol, preferably 1.3 to 1.8 mol, in each case per mol of zirconium.

Preferred perspiration-inhibiting salts are aluminum zirconium tetrachlorohydrate (Al:Zr=2 to 6; M:Cl=0.9 to 1.3), in particular salts having a molar metal-to-chloride ratio from 0.9 to 1.1, preferably 0.9 to 1.0.

Also preferred according to the present invention are aluminum zirconium chlorohydrate glycine salts that are stabilized with betaine $((CH_3)_3N^+\text{—}CH_2\text{—}COO^-)$. Particularly preferred corresponding compounds have a molar ratio of (total [betaine+glycine]) to Zr from (0.1 to 3.0):1, preferably (0.7 to 1.5):1, and a molar ratio of betaine to glycine of at least 0.001:1. Corresponding compounds are disclosed, for example, in U.S. Pat. No. 7,105,691.

A first obligatory component of the emulsifier system according to the present invention is a surface-active compound having an HLB value in the range from 9 to 15 that is selected from the partial esters of a polyglycerol that comprises 3, 4, or 5 glycerol units with a linear or branched, saturated or unsaturated carboxylic acid having 8 to 22 carbon atoms and with an organic edible acid, and that is included in a total quantity from 0.1 to 2 wt %, preferably 0.3 to 1.5 wt %, particularly preferably 0.5 to 1.1 wt %, extraordinarily preferably 0.6 to 0.8 wt %, based in each case on the total weight of the composition.

"Organic edible acids" are understood, in the food sector and for purposes of the present Application, as the following organic acids that, for example because of their acidic taste or their buffering effect or complexing action in the context of food production and preparation, may be used or are naturally included in foods: citric acid, adipic acid, hydroxysuccinic acid, succinic acid, lactic acid, and tartaric acid. An organic edible acid preferred according to the present invention that is esterified with the polyglycerol having 3, 4, or 5 glycerol units is citric acid.

Compositions preferred according to the present invention are therefore characterized in that they include at least one surface-active compound b) having an HLB value in the range from 9 to 15 that is selected from the partial esters of a polyglycerol that comprises 3, 4, or 5 glycerol units with a linear or branched, saturated or unsaturated carboxylic acid having 8 to 22 carbon atoms and with citric acid.

Particularly advantageous polyglycerol ester emulsifier agents having 3, 4, or 5 glycerol units b) having an HLB value in the range from 9 to 15 are those which are esterified not only with at least one edible acid, preferably with citric acid, but further with a linear or branched, saturated or unsaturated carboxylic acid having 8 to 22 carbon atoms, that is preferably selected from 2-ethylhexanoic acid, n-octanoic acid, n-decanoic acid, n-dodecanoic acid, n-tetradecanoic acid, n-hexadecanoic acid (palmitic acid), n-octadecanoic acid (stearic acid), isostearic acid, 12-hydroxystearic acid, oleic acid, linoleic acid, linolenic acid, n-eicosanoic acid, and n-docosanoic acid, each having a terminal acid group (i.e. with the carboxyl group in the alpha-position), wherein esterification with stearic acid is particularly preferred.

Further compositions preferred according to the present invention are therefore characterized in that the at least one surface-active compound b) having an HLB value in the range from 9 to 15 is selected from partial esters of a polyglycerol that comprises 3, 4, or 5 glycerol units with citric acid, and with a linear or branched, saturated or unsaturated carboxylic acid having 8 to 22 carbon atoms, that is preferably selected from 2-ethylhexanoic acid, n-octanoic acid, n-decanoic acid, n-dodecanoic acid, n-tetradecanoic acid, n-hexadecanoic acid (palmitic acid), n-octadecanoic acid (stearic acid), isostearic acid, 12-hydroxystearic acid, oleic acid, linoleic acid, linolenic acid, n-eicosanoic acid, and n-docosanoic acid, each having a terminal acid group (i.e. with the carboxyl group in the alpha-position), wherein esterification with stearic acid is particularly preferred.

Further particularly advantageous polyglycerol emulsifier agents b) having an HLB value in the range from 9 to 15, which are esterified as above, comprise 3 glycerol units.

Further compositions preferred according to the present invention are therefore characterized in that the at least one surface-active compound b) having an HLB value in the range from 9 to 15 is selected from partial esters of a polyglycerol that comprises 3 glycerol units with citric acid, and with a linear or branched, saturated or unsaturated carboxylic acid having 8 to 22 carbon atoms, that is preferably selected from 2-ethylhexanoic acid, n-octanoic acid, n-decanoic acid, n-dodecanoic acid, n-tetradecanoic acid, n-hexadecanoic acid (palmitic acid), n-octadecanoic acid (stearic acid), isostearic acid, 12-hydroxystearic acid, oleic acid, linoleic acid, linolenic acid, n-eicosanoic acid, and n-docosanoic acid, each having a terminal acid group (i.e. with the carboxyl group in the alpha-position), wherein esterification with stearic acid is particularly preferred.

The polyglycerol emulsifier agent b) has an HLB value in the range from 9 to 15. It has proven particularly advantageous, for the viscosity and the temperature stability of the emulsions according to the present invention at 40° C., if the polyglycerol emulsifier agent b) has an HLB value in the range from 10 to 14, particularly preferably 11 to 12.5.

In order to obtain a hydrophilic polyglycerol ester emulsifier agent that is esterified as presented above, the OH groups of the polyglycerol, preferably of the triglycerol, must not all be esterified with a linear or branched, saturated or unsaturated carboxylic acid having 8 to 22 carbon atoms or with citric acid. Corresponding polyglycerol ester emulsifier agents suitable according to the present invention are commercially obtainable. Particularly preferably, the at least one surface-active compound b) having an HLB value in the range from 9 to 15 is selected from partial esters of a polyglycerol that comprises 3 glycerol units with citric acid and with stearic acid, that carry the INCI name Polyglyceryl-3 Dicitrate/Stearate or Polyglyceryl-3 Stearate/Dicitrate. A commercial product of this kind is, for example, Tego Care PSC 3 of Evonik.

Further compositions preferred according to the present invention are therefore characterized in that the at least one surface-active compound b) having an HLB value in the range from 9 to 15 is selected from partial esters of a polyglycerol that comprises 3 glycerol units with citric acid and with stearic acid, that carry the INCI name Polyglyceryl-3 Dicitrate/Stearate or Polyglyceryl-3 Stearate/Dicitrate.

The HLB value is determined according to the present invention as described by Griffin, using the formula:
$HLB=20*(M_h/M)$, where $M_h$ is the molar mass of the hydrophilic portion of a molecule and M is the molar mass of the entire molecule. This results in a scale from 0 to 20.

A second obligatory component of the emulsifier agent system according to the present invention is, in a total quantity from 0.1 to 2.0 wt %, preferably 0.3 to 1.2 wt %, particularly preferably 0.6 to 1.1 wt %, extraordinarily preferably 0.8 to 1.0 wt %, at least one N-acyl-L-glutamic acid sodium salt of formula (GLUT-1)

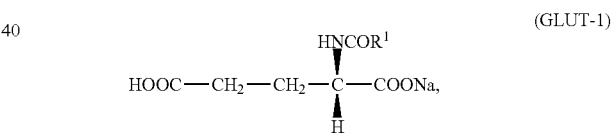

(GLUT-1)

in which $R^1CO$ represents a linear or branched, saturated or unsaturated acyl group having 6 to 22 carbon atoms, preferably having 8 to 18 carbon atoms.

Compositions preferred according to the present invention include at least one N-acyl-L-glutamic acid sodium salt of formula (GLUT-1) that is selected from compounds in which $R^1CO$ represents an n-hexanoyl, n-octanoyl, n-decanoyl, n-lauroyl, myristoyl, palmitoyl, stearoyl, arachidoyl, behenoyl, or cocoyl group, preferably a stearoyl group, in each case having a terminal carbonyl group. N-stearoylmonosodium-L-glutamate is extraordinarily preferred. This emulsifier agent is obtainable, for example, as a commercial product Eumulgin SG of BASF.

For the particularly preferred administration form of the compositions according to the present invention as a roll-on, a viscosity that is not too high is necessary. Preferred compositions according to the present invention are therefore characterized by a dynamic viscosity in the range from 300 to 10,000 mPas, preferably 800 to 7500 mPas, particularly preferably 1000 to 5000 mPas, measured with a Brookfield viscometer, spindle RV 4, 20 s$^{-1}$, no Helipath, at 20° C. ambient temperature and 20° C. sample temperature.

Both the resulting viscosity of the composition and its temperature stability at 40° C. are dependent, inter alia, on the weight ratio of polyglycerol ester b) to the N-acyl-L-glutamic acid sodium salt of formula (GLUT-1), based in each case on the total weights thereof.

Viscosities particularly suitable for roll-ons, as well as outstanding temperature stability at 40° C., are achieved when the weight ratio of the total weight of polyglycerol ester b) to the total weight of N-acyl-L-glutamic acid sodium salt of formula (GLUT-1) is in the range from 0.5 to 1.0, preferably 0.6 to 0.8. Preferred compositions according to the present invention are therefore characterized by a weight ratio of the total weight of polyglycerol ester b) to the total weight of N-acyl-L-glutamic acid sodium salt of formula (GLUT-1) in the range from 0.5 to 1.0, preferably 0.6 to 0.8.

As a further obligatory component the compositions according to the present invention include at least one cosmetic oil, liquid under standard conditions, that is not a fragrance and not an essential oil, in a total quantity from 0.5 to 10 wt %, preferably 1 to 8 wt %, particularly preferably 1.5 to 6 wt %, extraordinarily preferably 2 to 4.5 wt %, based in each case on the weight of the composition.

The cosmetic oil is liquid under standard conditions. The cosmetic oils liquid under standard conditions are not miscible with water. "Essential oils" are understood according to the present invention as volatile components that are produced by steam distillation of vegetable raw materials, for example citrus oils. When a "cosmetic oil" is discussed in the present Application, this always refers to a cosmetic oil that is not a fragrance and not an essential oil, is liquid under standard conditions, and is not miscible with water.

A distinction is made in the context of cosmetic oils between volatile and nonvolatile oils. "Nonvolatile" oils are understood as those oils that, at 20° C. and an ambient pressure of 1013 hPa, have a vapor pressure of less than 2.66 Pa (0.02 mm Hg). "Volatile" oils are understood as those oils that, at 20° C. and an ambient pressure of 1013 hPa, have a vapor pressure from 2.66 Pa to 40,000 Pa (0.02 mm to 300 mm Hg), preferably 10 to 12,000 Pa (0.1 to 90 mm Hg), particularly preferably 13 to 3000 Pa, extraordinarily preferably 15 to 500 Pa.

Volatile cosmetic oils are usually selected from among cyclic silicone oils having the INCI name Cyclomethicone. The INCI name Cyclomethicone is understood in particular to mean cyclotrisiloxane (hexamethylcyclotrisiloxane), cyclotetrasiloxane (octamethylcyclotetrasiloxane), cyclopentasiloxane (decamethylcyclopentasiloxane), and cyclohexasiloxane (dodecamethylcyclohexasiloxane). These oils have a vapor pressure of approx. 13 to 15 Pa at 20° C.

Cyclomethicones are known in the existing art as oils well suited for cosmetic compositions, in particular for deodorizing compositions. Because of their persistence in the environment, however, it can be preferred according to the present invention to omit the use of cyclomethicones. In an especially preferred embodiment, the compositions according to the present invention and used according to the present invention include 0 to less than 1 wt %, preferably a maximum of 0.1 wt % cyclomethicone, based on the weight of the composition.

A cyclomethicone replacement substance preferred according to the present invention is a mixture of $C_{13}$ to $C_{16}$ isoparaffins, $C_{12}$ to $C_{14}$ isoparaffins, and $C_{13}$ to $C_{15}$ alkanes whose viscosity at 25° C. is in the range from 2 to 6 mPas and which has a vapor pressure at 20° C. in the range from 10 to 150 Pa, preferably 100 to 150 Pa. A mixture of this kind is obtainable, for example, from Presperse Inc. under the name SiClone SR-5.

Further preferred silicone oils are selected from volatile linear silicone oils, in particular volatile linear silicone oils having 2 to 10 siloxane units, such as hexamethyldisiloxane ($L_2$), octamethyltrisiloxane ($L_3$), decamethyltetrasiloxane ($L_4$), as included e.g. in the commercial products DC 2-1184, Dow Corning® 200 (0.65 cSt), and Dow Corning® 200 (1.5 cSt) of Dow Corning, and low-molecular-weight Phenyl Trimethicone having a vapor pressure at 20° C. of approximately 2000 Pa, as obtainable e.g. from GE Bayer Silicones/Momentive under the name Baysilone Fluid PD 5.

Preferred antiperspirant compositions according to the present invention contain, because of the drier skin feel and faster active-agent release, at least one volatile silicone oil, which can be cyclic or linear.

Further preferred compositions according to the present invention contain, because of the drier skin feel and faster release of the antiperspirant active agent, at least one volatile non-silicone oil. Preferred volatile non-silicone oils are selected from $C_8$ to $C_{16}$ isoparaffins, in particular from isononane, isodecane, isoundecane, isododecane, isotridecane, isotetradecane, isopentadecane, and isohexadecane, as well as mixtures thereof. $C_{10}$ to $C_{13}$ isoparaffin mixtures, in particular those having a vapor pressure at 20° C. from 10 to 400 Pa, preferably 13 to 100 Pa, are preferred.

This at least one $C_8$ to $C_{16}$ isoparaffin is included preferably in a total quantity from 0.5 to 10 wt %, preferably 1 to 8 wt %, particularly preferably 1.5 to 6 wt %, extraordinarily preferably 2 to 4.5 wt %, based in each case on the total weight of the composition.

Further compositions preferred according to the present invention include at least one nonvolatile cosmetic oil selected from nonvolatile silicone oils and nonvolatile non-silicone oils. Residua of constituents insoluble in the composition, such as talc, but also the antiperspirant active agents (=perspiration-inhibiting aluminum salts) dried onto the skin, can be successfully masked with a nonvolatile oil. In addition, using a mixture of various oils, in particular of nonvolatile and volatile oil, parameters such as skin feel, visibility of residua, and stability of the composition according to the present invention can be precisely regulated and better adapted to consumers' needs.

Agents preferred according to the present invention are characterized in that the cosmetic oil that is not a fragrance and not an essential oil encompasses at least one volatile oil having a vapor pressure from 10 to 3000 Pa at 20° C. that is not a fragrance and not an essential oil, in a total quantity from 10 to 100 wt %, particularly preferably 30 to 80 wt %, based in each case on the total weight of the cosmetic oils.

It is of course likewise possible to formulate agents according to the present invention having a small proportion of volatile oils—i.e. having 0.5 to 15 wt % volatile oils, based on the total weight of the agent—or even having no volatile oils.

Oils particularly preferred according to the present invention are esters of linear or branched, saturated or unsaturated fatty alcohols having 2 to 30 carbon atoms with linear or branched, saturated or unsaturated fatty acids having 2 to 30 carbon atoms, which can be hydroxylated. Be it noted in this regard that some esters of linear or branched $C_1$ to $C_{22}$ alkanols or $C_{14}$ to $C_{22}$ alkenols, and some triesters of glycerol with linear or branched $C_2$ to $C_{22}$ carboxylic acids, which can be saturated or unsaturated, are solid under standard conditions, for example cetyl stearate or glycerol tristearate (=stearin). These esters that are solid under standard conditions do not represent cosmetic oils according to the present invention, since they do not meet the "liquid under standard conditions" criterion. The categorization as to whether such an ester is liquid or solid under standard conditions is a matter of the general knowledge of one skilled in the art.

Esters of linear or branched saturated fatty alcohols having 2 to 5 carbon atoms with linear or branched, saturated or unsaturated fatty acids having 3 to 18 carbon atoms, which can be hydroxylated, are preferred. Preferred examples thereof are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate, and 2-ethylhexyl stearate. Also preferred are isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid 2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, ethylene glycol dipalmitate, n-hexyl laurate, n-decyl oleate, oleyl oleate, oleyl erucate, erucyl oleate, $C_{12}$ to $C_{15}$ alkyl lactate, and di-$C_{12}$ to $C_{13}$ alkyl malate, as well as benzoic acid esters of linear or branched $C_{8-22}$ alkanols. Benzoic acid $C_{12}$ to $C_{15}$ alkyl esters are particularly preferred, obtainable e.g. as a commercial product Finsolv® TN($C_{12}$ to $C_{15}$ alkyl benzoate), as well as benzoic acid isostearyl esters, obtainable e.g. as Finsolv® SB, 2-ethylhexyl benzoate, obtainable e.g. as Finsolv® EB, and benzoic acid 2-octyldodecyl esters, obtainable e.g. as Finsolv® BOD.

Further oil components preferred according to the present invention are selected from $C_8$ to $C_{22}$ fatty alcohol esters of monovalent or polyvalent $C_2$ to $C_7$ hydroxycarboxylic acids, in particular esters of glycolic acid, lactic acid, malic acid, tartaric acid, citric acid, and salicylic acid. Such esters based on linear $C_{14/15}$ alkanols, e.g. $C_{12}$ to $C_{15}$ alkyl lactate, and on $C_{12/13}$ alkanols branched in the 2-position, can be obtained under the trade name Cosmacol from Nordmann, Rassmann GmbH & Co., Hamburg, in particular the commercial products Cosmacol® ESI, Cosmacol® EMI, and Cosmacol® ETI.

The use of isopropyl esters of $C_{12}$ to $C_{18}$ carboxylic acids, in particular the use of isopropyl myristate, and particularly preferably mixtures of isopropyl myristate with $C_{10}$ to $C_{13}$ isoparaffin mixtures, the latter preferably having a vapor pressure from 10 to 400 Pa at 20° C., has proven particularly advantageous, for example in terms of active-agent release.

Agents preferred according to the present invention include at least one ester of linear or branched, saturated or unsaturated fatty alcohols having 2 to 30 carbon atoms with linear or branched, saturated or unsaturated fatty acids having 2 to 30 carbon atoms, which can be hydroxylated, in a total quantity from 0.5 to 10 wt %, preferably 1 to 8 wt %, particularly preferably 1.5 to 6 wt %, extraordinarily preferably 2 to 4.5 wt %, based in each case on the weight of the total composition.

A further particularly preferred ester oil is triethyl citrate. Further products preferred according to the present invention include triethyl citrate and at least one $C_8$ to $C_{16}$ isoparaffin selected from isononane, isodecane, isoundecane, isododecane, isotridecane, isotetradecane, isopentadecane, and isohexadecane, as well as mixtures of said isoparaffins. Further products preferred according to the present invention include triethyl citrate and at least one $C_8$ to $C_{16}$ isoparaffin selected from isononane, isodecane, isoundecane, isododecane, isotridecane, as well as mixtures of said $C_8$ to $C_{16}$ isoparaffins. Further products preferred according to the present invention include triethyl citrate and a mixture of isodecane, isoundecane, isododecane, and isotridecane.

Further nonvolatile non-silicone oils preferred according to the present invention are selected from branched saturated or unsaturated fatty alcohols having 6 to 30 carbon atoms. These alcohols are often also referred to as "Guerbet alcohols," since they are obtainable via the Guerbet reaction. Preferred alcohol oils are 2-hexyldecanol, 2-octyldodecanol, and 2-ethyhexyl alcohol. Isostearyl alcohol is likewise preferred. Further preferred nonvolatile oils are selected from mixtures of Guerbet alcohols and Guerbet alcohol esters, e.g. 2-hexyldecanol and 2-hexyldecyl laurate.

The term "triglyceride" used below means "glycerol triester." Further nonvolatile oils preferred according to the present invention are selected from triglycerides of linear or branched, saturated or unsaturated, optionally hydroxylated $C_{8-30}$ fatty acids, provided they are liquid under standard conditions. The use of natural oils, e.g. soy oil, cottonseed oil, sunflower oil, palm oil, palm kernel oil, linseed oil, almond oil, castor oil, corn oil, rapeseed oil, olive oil, sesame oil, thistle oil, wheat germ oil, peach-kernel oil, and the liquid components of coconut oil and the like, can be particularly suitable. Synthetic triglyceride oils are particularly preferred, in particular Capric/Caprylic Triglycerides, e.g. the commercial products Myritol® 318 or Myritol® 331 (BASF/BASF) having unbranched fatty acid esters, as well as glyceryl triisostearin and glyceryl tri(2-ethylhexanoate) having branched fatty acid esters. Triglyceride oils of this kind preferably account for a proportion of less than 50 wt % of the total weight of all cosmetic oils in the composition according to the present invention. Particularly preferably, the total weight of triglyceride oils is 0.1 to wt %, preferably 0.2 to 1 wt %, particularly preferably 0.5 to 0.8 wt %, based in each case on the total composition.

Further nonvolatile non-silicone oils particularly preferred according to the present invention are selected from dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further nonvolatile non-silicone oils particularly preferred according to the present invention are selected from symmetrical, asymmetrical, or cyclic esters of carbonic acid with $C_6$ to $C_{20}$ alcohol, e.g. di-n-caprylyl carbonate (Cetiol® CC) or di-(2-ethylhexyl) carbonate (Tegosoft DEC). Esters of carbonic acid with $C_1$ to $C_5$ alcohols, e.g. glycerol carbonate or propylene carbonate, however, are not compounds suitable as a cosmetic oil.

Further cosmetic oils that are particularly preferred according to the present invention are selected from nonvolatile silicone oils. Nonvolatile silicone oils preferred according to the present invention are selected from linear polyalkylsiloxanes having a kinematic viscosity at 25° C. of at least 5 cSt to 2000 cSt, selected in particular from linear polydimethylsiloxanes having a kinematic viscosity at 25° C. from 5 cSt to 2000 cSt, preferably 10 to 350 cSt, particularly preferably 50 to 100 cSt, such as those obtainable e.g. under the commercial names Dow Corning® 200 or Xiameter PMX from Dow Corning and Xiameter, respectively. Further preferred nonvolatile silicone oils are Phenyl Trimethicone having a kinematic viscosity at 25° C. from 10 to 100 cSt, preferably from 15 to 30 cSt, and cetyl dimethicones.

Natural and synthetic hydrocarbons preferred according to the present invention are selected from paraffin oils, isohexadecane, isoeicosane, polyisobutenes, and polydecenes, which are obtainable e.g. under the name Emery® 3004, 3006, 3010 or under the name Nexbase® 2004G from Nestle, as well as 1,3-di-(2-ethylhexyl)cyclohexane.

As a further obligatory component, the compositions according to the present invention include at least one hydrogel-forming polymer in a total quantity from 0.08 to 1 wt %, preferably 0.1 to 0.8 wt %, particularly preferably 0.15 to 0.6 wt %, extraordinarily preferably 0.2 to 0.4 wt %, based in each case on the weight of the composition.

Hydrogel-forming polymers preferred according to the present invention are selected from cellulose ethers, principally hydroxyalkyl celluloses, in particular hydroxypropyl cellulose, hydroxypropylmethyl cellulose, hydroxyethyl cellulose, carboxymethyl cellulose, cetylhydroxyethyl cellulose, hydroxybutylmethyl cellulose, methylhydroxyethyl cellulose, furthermore xanthan gum, sclerotium gum, succinoglucans, polygalactomannans, in particular guar gums and locust bean gum, in particular guar gum and locust bean gum themselves and nonionic hydroxyalkyl guar derivatives and locust bean gum derivatives, such as hydroxypropyl guar, carboxymethylhydroxypropyl guar, hydroxypropylmethyl guar, hydroxyethyl guar, and carboxymethyl guar, furthermore pectins, agar, carrageenan, tragacanth, gum arabic, karaya gum, tara gum, gellan, gelatin, casein, propylene glycol alginate, alginic acids and salts thereof, in particular sodium alginate, potassium alginate, and calcium alginate, furthermore polyvinylpyrrolidones, polyvinyl alcohols, polyacrylamides. The at least one hydrogel former can furthermore (although less preferably) be selected from physically modified (e.g. by pregelatinization) and/or chemically modified starches, in particular hydroxypropylated starch phosphates and starch octenylsuccinates and aluminum, calcium, or sodium salts thereof, furthermore (again less preferably) from acrylic acid-acrylate copolymers, acrylic acid-acrylamide copolymers, acrylic acid-vinylpyrrolidone copolymers, acrylic acid-vinyl-formamide copolymers, and polyacrylates.

Particularly preferred hydrogel-forming polymers are selected from cellulose ethers, principally from hydroxyalkyl celluloses, in particular from hydroxypropyl cellulose, hydroxypropylmethyl cellulose, hydroxyethyl cellulose, carboxymethyl cellulose, cetylhydroxyethyl cellulose, hydroxybutylmethyl cellulose, and methylhydroxyethyl cellulose, as well as mixtures thereof. An extraordinarily preferred hydrogel-forming agent is hydroxyethyl cellulose. Compositions extraordinarily preferred according to the present invention include hydroxyethyl cellulose in a total quantity from 0.08 to 1 wt %, preferably 0.1 to 0.8 wt %, particularly preferably 0.15 to 0.6 wt %, extraordinarily preferably 0.2 to 0.4 wt %, based in each case on the weight of the composition. Further compositions extraordinarily preferred according to the present invention include hydroxyethyl cellulose as the only hydrogel-forming agent, in a total quantity from 0.08 to 1 wt %, preferably 0.1 to 0.8 wt %, particularly preferably 0.15 to 0.6 wt %, extraordinarily preferably 0.2 to 0.4 wt %, based in each case on the weight of the composition.

As a further obligatory component the compositions according to the present invention contain, in a total quantity from 0.05 to 4 wt %, preferably 0.5 to 3.5 wt %, particularly preferably 1 to 3 wt %, and extraordinarily preferably 1.5 to 2.5 wt %, at least one structuring agent that is selected from linear saturated 1-alkanols having 14 to 22 carbon atoms, glyceryl mono- and diesters of linear or branched, saturated or unsaturated carboxylic acids having 8 to 22 carbon atoms, linear saturated 1-alkanecarboxylic acids having 14 to 22 carbon atoms, mono- and diesters of ethylene glycol with linear saturated and unsaturated fatty acids having 12 to 30, in particular 14 to 22 carbon atoms, the mono-, di-, tri-, and tetraesters of pentaerythritol with linear saturated and unsaturated fatty acids having 12 to 30, in particular 14 to 22 carbon atoms, as well as mixtures of said structuring agents, wherein the quantity indications refer to the weight of the composition.

The term "structuring agent" is understood for purposes of the present Application as a nonionic water-in-oil emulsifier agent having an HLB value greater than 1.0 and less than or equal to 7.0 that builds up in the emulsion, which can elevate viscosity or contribute to stabilization of the emulsion. This can occur via the formation of wax particles, solidification of the oil phase, or formation of liquid-crystal, in particular lamellar, phases.

Structuring agents particularly preferred according to the present invention are selected from linear saturated 1-alkanols having 14 to 22 carbon atoms, in particular from myristyl alcohol, cetyl alcohol, stearyl alcohol, arachyl alcohol, and behenyl alcohol, and from mixtures of said 1-alkanols. Stearyl alcohol, cetyl alcohol, and mixtures of these 1-alkanols, which are also referred to as "cetearyl alcohol," are extraordinarily preferred. Stearyl alcohol has proven to be particularly advantageous for the temperature stability of the emulsions according to the present invention at 40° C., in particular stearyl alcohol in a quantity from 1 to 3 wt % based on the weight of the composition.

Further structuring agents particularly preferred according to the present invention are selected from glyceryl mono- and diesters of linear or branched, saturated or unsaturated carboxylic acids having 8 to 22 carbon atoms, in particular from glyceryl monostearate, glyceryl distearate, glyceryl monocaprinate, glyceryl dicaprinate, glyceryl monocaprylate, glyceryl dicaprylate, glyceryl monolaurate, glyceryl dilaurate, glyceryl monomyristate, glyceryl dimyristate, glyceryl monopalmitate, glyceryl dipalmitate, glyceryl mono-12-hydroxystearate, glyceryl di-12-hydroxystearate, glyceryl monooleate, glyceryl dioleate, glyceryl monolanolate, glyceryl dilanolate, glyceryl monoisostearate, and glyceryl diisostearate, as well as mixtures of these glyceryl esters. From this class of structuring agents, glyceryl monostearate, glyceryl distearate, glyceryl monopalmitate, and glyceryl dipalmitate, as well as mixtures of these glyceryl esters, are extraordinarily preferred.

Glyceryl monostearate, glyceryl distearate, and mixtures of glyceryl monostearate and glyceryl distearate have likewise proven to be particularly advantageous for the temperature stability of the emulsions according to the present invention at 40° C., in particular mixtures of glyceryl monostearate and glyceryl distearate in a quantity from 1 to 3 wt % based on the weight of the composition.

Further structuring agents preferred according to the present invention are selected from linear saturated 1-alkanecarboxylic acids having 14 to 22 carbon atoms, in particular from myristic acid, palmitic acid, stearic acid, arachidic acid, and behenic acid, and from mixtures of these 1-alkanecarboxylic acids.

Further structuring agents preferred according to the present invention are selected from mono- and diesters of ethylene glycol with linear saturated and unsaturated fatty acids having 12 to 30, in particular 14 to 22 carbon atoms, in particular from ethylene glycol monostearate, ethylene glycol distearate, ethylene glycol monocaprinate, ethylene glycol dicaprinate, ethylene glycol monocaprylate, ethylene glycol dicaprylate, ethylene glycol monolaurate, ethylene glycol dilaurate, ethylene glycol monomyristate, ethylene glycol dimyristate, ethylene glycol monopalmitate, ethylene glycol dipalmitate, ethylene glycol mono-12-hydroxystearate, ethylene glycol di-12-hydroxystearate, ethylene glycol monooleate, ethylene glycol dioleate, ethylene glycol monolanolate, and ethylene glycol dilanolate, as well as mixtures of these ethylene glycol esters. Ethylene glycol distearate, ethylene glycol monostearate, and mixtures of these two ethylene glycol esters are particularly preferred.

Further structuring agents preferred according to the present invention are selected from the mono-, di-, tri-, and tetraesters of pentaerythritol with linear saturated and unsaturated fatty acids having 12 to 30, in particular 14 to 22 carbon atoms, selected in particular from pentaerythrityl monostearate, pentaerythrityl distearate, pentaerythrityl monocaprinate, pentaerythrityl dicaprinate, pentaerythrityl monocaprylate, pentaerythrityl dicaprylate, pentaerythrityl monolaurate, pentaerythrityl dilaurate, pentaerythrityl monomyristate, pentaerythrityl dimyristate, pentaerythrityl monopalmitate, pentaerythrityl dipalmitate, pentaerythrityl mono-12-hydroxystearate, pentaerythrityl di-12-hydroxystearate, pentaerythrityl monooleate, pentaerythrityl dioleate, pentaerythrityl monolanolate, and pentaerythrityl dilanolate, as well as mixtures of these pentaerythritol esters. Pentaerythrityl distearate and pentaerythrityl monostearate, as well as mixtures of these pentaerythritol esters, are particularly preferred, in particular mixtures having pentaerythrityl tristearate and/or pentaerythrityl tetrastearate.

As a further obligatory component the compositions according to the present invention include water in a total quantity from 30 to 90 wt %, preferably 40 to 80 wt %, particularly preferably 60 to 78 wt %, extraordinarily preferably 65 to 73 wt %, based in each case on the weight of the composition.

For purposes of the present Application, the quantity of water of crystallization, water of hydration, or similarly molecularly bound water that is included in the constituents used, in particular in the perspiration-inhibiting active agents, does not represent free water, and is therefore not taken into account when calculating the aforementioned water content of the composition.

In a preferred embodiment of the invention, a portion of the water is replaced by a water-soluble solvent such as, in particular, ethanol, 1,2-propylene glycol, glycerol, 1,3-butylene glycol, and/or similar glycols, and mixtures of said solvents. A water content from 45 to 58 wt %, preferably 50 to 55 wt %, based in each case on the weight of the composition, can therefore be preferred.

The composition of some preferred oil-in-water emulsions according to the present invention can be gathered from the tables below. The quantity indications always refer to the total weight of the respective component in the composition (wt %).

| | 1 | 2 | 3 | 4 |
|---|---|---|---|---|
| Perspiration-inhibiting aluminum salt | 2-40 wt % | 8-35 | 10-28 | 12-20 |
| Partial ester of tri-, tetra-, or pentaglycerol with linear saturated C8-22 alkanoic acid and edible acid, HLB 9-5 | 0.1-2 | 0.3-1.5 | 0.5-1.1 | 0.6-0.8 |
| At least one N-acyl-L-glutamic acid sodium salt of formula (GLUT-1) | 0.1-2.0 | 0.3-1.2 | 0.6-1.1 | 0.8-1.0 |
| Cosmetic oil | 0.5-10 | 1-8 | 1.5-6 | 2-4.5 |
| At least one hydrogel-forming polymer | 0.08-1 | 0.1-0.8 | 0.15-0.6 | 0.2-0.4 |
| At least one structuring agent per Claim 1 | 0.05-4 | 0.5-3.5 | 1-3 | 1.5-2.5 |
| Water | 30-90 | 40-80 | 60-78 | 65-73 |

| | 5 | 6 | 7 |
|---|---|---|---|
| Perspiration-inhibiting aluminum salt | 2-40 wt % | 8-35 | 10-28 |
| Partial ester of tri-, tetra-, or pentaglycerol with linear saturated C8-22 alkanoic acid and edible acid, HLB 9-5 | 0.1-2 | 0.3-1.5 | 0.5-1.1 |
| At least one N-acyl-L-glutamic acid sodium salt of formula (GLUT-1) | 0.1-2.0 | 0.3-1.2 | 0.6-1.1 |
| Cosmetic oil | 0.5-10 | 1-8 | 2-4.5 |
| At least one hydrogel-forming polymer | 0.08-1 | 0.1-0.8 | 0.2-0.4 |
| At least one structuring agent per Claim 1 | 0.05 to 4 | 0.5-3.5 | 1-3 |
| Water | 30-90 | 40-80 | 60-78 |

| | 8 | 9 | 10 | 11 |
|---|---|---|---|---|
| Perspiration-inhibiting aluminum salt | 2-40 wt % | 8-35 | 10-28 | 12-20 |
| Partial ester of tri-, tetra-, or pentaglycerol with linear saturated C8-22 alkanoic acid and edible acid, HLB 9-5 | 0.1-2 | 0.3-1.5 | 0.5-1.1 | 0.6-0.8 |
| At least one N-acyl-L-glutamic acid sodium salt of formula (GLUT-1) | 0.1-2.0 | 0.3-1.2 | 0.6-1.1 | 0.8-1.0 |
| Wt. ratio of total wt. of polyglycerol ester b) to total weight of N-acyl-L-glutamic acid sodium salt of formula (GLUT-1) | 0.5-1.0 | 0.5-1.0 | 0.6-0.8 | 0.6-0.8 |
| Cosmetic oil | 0.5-10 | 1-8 | 1.5-6 | 2-4.5 |
| At least one hydrogel-forming polymer | 0.08-1 | 0.1-0.8 | 0.15-0.6 | 0.2-0.4 |
| At least one structuring agent per | 0.05 to 4 | 0.5-3.5 | 1-3 | 1.5-2.5 |

| Claim 1 | | | | |
|---|---|---|---|---|
| Water | 30-90 | 40-80 | 60-78 | 65-73 |

| | 12 | 13 | 14 | 15 |
|---|---|---|---|---|
| Perspiration-inhibiting aluminum salt | 2-40 wt % | 8-35 | 10-28 | 12-20 |
| Polyglyceryl-3 Dicitrate/Stearate | 0.1-2 | 0.3-1.5 | 0.5-1.1 | 0.6-0.8 |
| Sodium N-stearoyl-L-glutamate | 0.1-2.0 | 0.3-1.2 | 0.6-1.1 | 0.8-1.0 |
| Cosmetic oil | 0.5-10 | 1-8 | 1.5-6 | 2-4.5 |
| Hydroxyethyl cellulose | 0.08-1 | 0.1-0.8 | 0.15-0.6 | 0.2-0.4 |
| Stearyl alcohol | 0.05 to 4 | 0.5-3.5 | 1-3 | 1.5-2.5 |
| Water | 30-90 | 40-80 | 60-78 | 65-73 |

| | 16 | 17 | 18 | 19 |
|---|---|---|---|---|
| Perspiration-inhibiting aluminum salt | 2-40 wt % | 8-35 | 10-28 | 12-20 |
| Polyglyceryl-3 Dicitrate/Stearate | 0.1-2 | 0.3-1.5 | 0.5-1.1 | 0.6-0.8 |
| Sodium N-stearoyl-L-glutamate | 0.1-2.0 | 0.3-1.2 | 0.6-1.1 | 0.8-1.0 |
| Wt. ratio of Polyglyceryl-3 Dicitrate/Stearate to sodium N-stearoyl-L-glutamate | 0.5-1.0 | 0.5-1.0 | 0.6-0.8 | 0.6-0.8 |
| Cosmetic oil | 0.5-10 | 1-8 | 1.5-6 | 2-4.5 |
| Hydroxyethyl cellulose | 0.08-1 | 0.1-0.8 | 0.15-0.6 | 0.2-0.4 |
| Stearyl alcohol | 0.05 to 4 | 0.5-3.5 | 1-3 | 1.5-2.5 |
| Water | 30-90 | 40-80 | 60-78 | 65-73 |

| | 20 | 21 | 22 |
|---|---|---|---|
| Perspiration-inhibiting aluminum salt | 2-40 wt % | 8-35 | 10-28 |
| Polyglyceryl-3 Dicitrate/Stearate | 0.1-2 | 0.3-1.5 | 0.5-1.1 |
| Sodium N-stearoyl-L-glutamate | 0.1-2.0 | 0.3-1.2 | 0.6-1.1 |
| Cosmetic oil | 0.5-10 | 1-8 | 2-4.5 |
| Hydroxyethyl cellulose | 0.08-1 | 0.1-0.8 | 0.2-0.4 |
| Stearyl alcohol | 0.05 to 4 | 0.5-3.5 | 1-3 |
| Water | 30-90 | 40-80 | 60-78 |

| | 23 | 24 | 25 |
|---|---|---|---|
| Perspiration-inhibiting aluminum salt | 2-40 wt % | 8-35 | 10-28 |
| Polyglyceryl-3 Dicitrate/Stearate | 0.1-2 | 0.3-1.5 | 0.5-1.1 |
| Sodium N-stearoyl-L-glutamate | 0.1-2.0 | 0.3-1.2 | 0.6-1.1 |
| Cosmetic oil | 0.5-10 | 1-8 | 2-4.5 |
| Hydroxyethyl cellulose | 0.08-1 | 0.1-0.8 | 0.2-0.4 |
| Stearyl alcohol | 0.05 to 4 | 0.5-3.5 | 1-3 |
| Water | 30-90 | 40-80 | 60-78 |
| Wt. ratio of Polyglyceryl-3 Dicitrate/Stearate to sodium N-stearoyl-L-glutamate | 0.5-1.0 | 0.5-1.0 | 0.6-0.8 |

Preferred compositions according to the present invention furthermore include at least one water-soluble polyvalent $C_2$ to $C_9$ alkanol having 2 to 6 hydroxyl groups, as well as mixtures thereof. A polyol of this kind not only improves the cosmetic care-providing properties of the compositions according to the present invention, but also acts to promote the temperature stability of the emulsion at 40° C. Polyols are preferably selected from 1,2-propylene glycol, glycerol, 2-methyl-1,3-propanediol, 1,2-butylene glycol, 1,3-butylene glycol, 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixtures of cis- and trans-1,4-dimethylolcyclohexane, as well as mixtures of the aforesaid substances. Particularly preferred compositions according to the present invention include at least one water-soluble polyvalent $C_2$ to $C_9$ alkanol having 2 to 6 hydroxyl groups in a total quantity from 0.5 to 14 wt %, preferably 2 to 11 wt %, particularly preferably 5 to 7 wt %, based in each case on the total weight of the composition.

Particularly preferred compositions according to the present invention furthermore include at least one fragrance. The definition of a "fragrance" for purposes of the present Application corresponds to the definition usual in the art, as may be gathered from the RÖMPP Chemie Lexikon [Chemical Lexicon] as of December 2007. According to the latter, a fragrance is a chemical compound having an odor and/or taste that excites the receptors of the hair cells of the olfactory system (adequate stimulus). The physical and chemical properties necessary for this are a low molar mass of at most 300 g/mol, a high vapor pressure, minimal water solubility and high lipid solubility, as well as weak polarity and the presence of at least one osmophoric group in the molecule. In order to distinguish volatile low-molecular-weight substances that are usually (and also for purposes of the present Application) regarded and utilized not as fragrances but instead principally as solvents, for example ethanol, propanol, isopropanol, and acetone, from fragrances according to the present invention, fragrances according to the present invention have a molar mass from 74 to 300 g/mol, include at least one osmophoric group in the molecule, and have an odor and/or taste, i.e. they excite the receptors of the hair cells of the olfactory system.

Perfumes, perfume oils, or perfume oil constituents can be used as fragrances. Perfume oils or scents can be, according to the present invention, individual fragrance compounds, e.g. synthetic products of the ester, ether, aldehyde, ketone, alcohol, and hydrocarbon types. Fragrance compounds of the ester type are, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate, and jasmecyclate. Ethers include, for example, benzyl ethyl ether and ambroxan; aldehydes, for example, the linear alkanals having 8 to 18 carbon atoms, citral, citronellal, citronellyloxyacetaldehyde, cyclamenaldehyde, lilial, and bourgeonal; ketones, for example, the ionones, alpha-isomethylionone and methyl cedryl ketone; alcohols include anethole, citronellol, eugenol, geraniol, linalool, phenylethyl alcohol, and the terpineols alpha-terpineol, beta-terpineol, gamma-terpineol, and delta-terpineol; and hydrocarbons include principally terpenes such as limonene and pinene. Preferably, however, mixtures of different fragrances that together produce an attractive scent note are used. The fragrances can also be included in encapsulated form. Particularly preferred compositions according to the present invention include at least one fragrance in a total quantity from 0.00001 to 10 wt %, preferably 0.5 to 7 wt %, extraordinarily preferably 1 to 6 wt %, based in each case on the total weight of the composition.

Further compositions preferred according to the present invention include at least one deodorant active agent in a total quantity from 0.001 to 10 wt %, preferably 0.2 to 7 wt %, particularly preferably 1 to 5 wt %, extraordinarily preferably 1.5 to 3 wt %, wherein the "wt %" indications refer to the total weight of the composition.

Ethanol is regarded according to the present invention not as a deodorant active agent but, if present, only as a constituent of the carrier.

In a preferred embodiment the agents according to the present invention include as a deodorizing active agent at least one silver salt that is preferably selected from silver sulfate, silver nitrate, silver citrate, silver dihydrogen citrate, silver lactate, silver acetate, silver malate, silver succinate, silver tartrate, silver mandelate, silver salicylate, silver gluconate, silver adipate, and silver galactarate, and from mixtures of said salts. Silver sulfate, silver citrate, silver dihydrogen citrate, and silver lactate, as well as mixtures of said salts, are extraordinarily preferred.

Further preferred compositions according to the present invention include at least one silver salt that is preferably selected from silver sulfate, silver nitrate, silver citrate, silver dihydrogen citrate, silver lactate, silver acetate, silver malate, silver succinate, silver tartrate, silver mandelate, silver salicylate, silver gluconate, silver adipate, and silver galactarate, and from mixtures of said salts, in quantities such that silver is included in a total quantity from 1 to 100 ppm, preferably 2 to 50 ppm, particularly preferably 5 to 20 ppm, extraordinarily preferably 7 to 10 ppm, based in each case on the weight of the composition. The correspondingly required quantity of silver salt(s) can be calculated based on the molar masses of silver (107.87 g/mol) and of the respective silver salts (silver lactate, for example, has a molar mass of 196.94 g/mol).

In a further preferred embodiment the compositions according to the present invention include as a deodorizing active agent at least one aromatic alcohol of structure (AA-1)

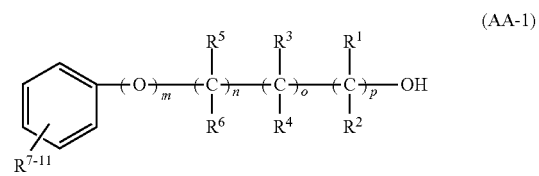

wherein residues $R^1$ to $R^6$ mutually independently denote a hydrogen atom, an alkyl group having 1 to 10 carbon atoms, which can be linear or branched and can be substituted with OH groups or alkoxy groups having 1 to 5 carbon atoms, or an alkenyl group having 2 to 10 carbon atoms, which can be linear or branched and can be substituted with OH groups or alkoxy groups having 1 to 5 carbon atoms, residues $R^7$ to $R^{11}$ mutually independently denote a hydrogen atom, a halogen atom, in particular a chlorine atom, or an alkyl group having 1 to 10 carbon atoms, which can be linear or branched and can be substituted with OH groups or alkoxy groups having 1 to 5 carbon atoms, in particular with a methoxy group, m=0 or 1, n, o, p mutually independently are integers from 0 to 10, wherein at least one of the values n, o, p is not equal to 0.

Particularly preferred products according to the present invention include at least one alcohol AA-1 as described above which is selected from anise alcohol, 2-methyl-5-phenylpentan-1-ol, 1,1-dimethyl-3-phenylpropan-1-ol, benzyl alcohol, 2-phenylethan-1-ol, 3-phenylpropan-1-ol, 4-phenylbutan-1-ol, 5-phenylpentan-1-ol, 2-benzylheptan-1-ol, 2,2-dimethyl-3-phenylpropan-1-ol, 2,2-dimethyl-3-(3'-methylphenyl)propan-1-ol, 2-ethyl-3-phenylpropan-1-ol, 2-ethyl-3-(3'-methylphenyl)propan-1-ol, 3-(3'-chlorophenyl)-2-ethylpropan-1-ol, 3-(2'-chlorophenyl)-2-ethylpropan-1-ol, 3-(4'-chlorophenyl)-2-ethylpropan-1-ol, 3-(3',4'-dichlorophenyl)-2-ethylpropan-1-ol, 2-ethyl-3-(2'-methylphenyl)propan-1-ol, 2-ethyl-3-(4'-methylphenyl)propan-1-ol, 3-(3',4'-dimethylphenyl)-2-ethylpropan-1-ol, 2-ethyl-3-(4'-methoxyphenyl)propan-1-ol, 3-(3',4'-dimethoxyphenyl)-2-ethylpropan-1-ol, 2-allyl-3-phenylpropan-1-ol, and 2-n-pentyl-3-phenylpropan-1-ol, as well as mixtures thereof. 2-Benzylheptan-1-ol, as well as mixtures of 2-benzylheptan-1-ol and phenoxyethanol, are extraordinarily preferred. Further particularly preferred compositions according to the present invention include at least one alcohol AA-1 as described above in a total quantity from 0.05 to 10 wt %, preferably 0.1 to 5 wt %, particularly preferably 0.2 to 2 wt %, extraordinarily preferably 0.3 to 1.5 wt %, based in each case on the weight of the composition. Extraordinarily preferred agents according to the present invention include 2-benzylheptan-1-ol in a total quantity from 0.05 to 1.5 wt %, preferably 0.1 to 1 wt %, particularly preferably 0.2 to 0.5 wt %, based in each case on the weight of the composition. The alcohols AA-1 can also be included in encapsulated form.

In a further preferred embodiment the compositions according to the present invention include as a deodorant active agent at least one 1,2-alkanediol having 5 to 12 carbon atoms, which can be described by the formula HO—$CH_2$—CH(OH)—$(CH_2)_n$—$CH_3$ in which n denotes the numbers 2, 3, 4, 5, 6, 7, 8, or 9, as well as mixtures of said 1,2-alkanediols. 1,2-Alkanediols having 5 to 12 carbon atoms that are particularly preferred according to the present invention are selected from 1,2-pentanediol, 1,2-hexanediol, 1,2-octanediol, 1,2-decanediol, and mixtures thereof. A very particularly preferred combination according to the present invention is mixtures of 1,2-hexanediol and 1,2-octanediol, preferably at a weight ratio from 10:1 to 1:10, more preferably from 5:1 to 1:5, particularly preferably at a weight ratio of 1:1. Preferred agents according to the present invention include at least one 1,2-alkanediol having 5 to 12 carbon atoms, which can be described by the formula HO—$CH_2$—CH(OH)—$(CH_2)_n$—$CH_3$ in which n denotes the numbers 2, 3, 4, 5, 6, 7, 8, or 9, in a total quantity from 0.2 to 15 wt %, preferably 0.3 to 10 wt %, particularly preferably 0.4 to 5 wt %, and extraordinarily preferably 0.5 to 2 wt %, based on each case on the weight of the composition. Extraordinarily preferred agents according to the present invention include 0.2 to 0.5 wt % 1,2-hexanediol and 0.2 to 0.5 wt % 1,2-octanediol, based in each case on the weight of the composition.

Further preferred agents according to the present invention are characterized by including the deodorant active agent 3-(2-ethylhexyloxy)-1,2-propanediol, preferably in a total quantity from 0.05 to 5 wt %, preferably 0.1 to 2 wt %, particularly preferably 0.2 to 1.5 wt %, extraordinarily preferably 0.5 to 1.0 wt %, based in each case on the weight of the composition.

Further preferred agents according to the present invention are characterized by including tropolone (2-hydroxy-2,4,6-cycloheptatrienone), preferably in a quantity from 0.001 to 0.1 wt % based on the weight of the composition.

Further preferred agents according to the present invention are characterized by including the deodorant active agent triethyl citrate. Triethyl citrate is a known deodorant active agent that acts as an enzyme inhibitor for esterases and lipases and thus contributes to the broadband action of agents according to the present invention. Preferred agents according to the present invention include 0.5 to 15 wt %, preferably 3 to 8 wt %, extraordinarily preferably 4 to 6 wt %, based in each case on the weight of the composition.

Compounds that inhibit at least one of the enzymes arylsulfatase, beta-glucuronidase, 5-lipoxygenase, or cystathionine beta-lyase likewise represent deodorant active agents preferred according to the present invention.

Further preferred compositions according to the present invention are characterized by including at least one compound that is an inhibitor of the enzyme arylsulfatase. Deodorant active agents preferred according to the present invention that act as an arylsulfatase inhibitor are those disclosed, for example, in U.S. Pat. No. 5,643,559, U.S. Pat. No. 5,676,937, WO 2001/099376 A2, EP 1430879 A1, and DE 10216368 A1. Further particularly preferred agents according to the present invention are characterized by including at least one compound that is an inhibitor of the enzyme arylsulfatase in a total quantity from 0.001 to 10 wt %, preferably 0.01 to 5 wt %, particularly preferably 0.1 to 2.5 wt %, based in each case on the weight of the composition.

Further preferred compositions according to the present invention are characterized by including at least one compound that is an inhibitor of the enzyme beta-glucuronidase. Deodorant active agents preferred according to the present invention that act as beta-glucuronidase inhibitors are those disclosed, for example, in WO 2003/039505 A2. Further particularly preferred agents according to the present invention are characterized by including at least one compound that is an inhibitor of the enzyme beta-glucuronidase in a total quantity from 0.001 to 10 wt %, preferably 0.01 to 5 wt %, particularly preferably 0.1 to 2.5 wt %, based in each case on the weight of the composition.

Further agents preferred according to the present invention are characterized by including at least one compound that is an inhibitor of the enzyme lipase. Deodorant active agents preferred according to the present invention that act as lipase inhibitors are selected from those that are disclosed in EP 1428520 A2, furthermore selected from the aminomethylenemalonic acid derivatives according to DE 3018132 A1, ethylene oxide-propylene oxide copolymers according to GB 2335596 A1, and salts of phytic acid according to EP 650 720 A1. Further particularly preferred agents according to the present invention are characterized by including at least one compound that is an inhibitor of the enzyme lipase in a total quantity from 0.001 to 10 wt %, preferably 0.01 to 5 wt %, particularly preferably 0.1 to 2.5 wt %, based in each case on the weight of the composition.

Further particularly preferred agents according to the present invention are characterized by including at least one compound that is an inhibitor of 5-lipoxygenase. Deodorant active agents preferred according to the present invention that act as 5-lipoxygenase inhibitors are disclosed in EP 1428519 A2. Further particularly preferred agents according to the present invention are characterized by including at least one compound that is an inhibitor of the enzyme 5-lipoxygenase in a total quantity from 0.001 to 10 wt %, preferably 0.01 to 5 wt %, particularly preferably 0.1 to 2.5 wt %, based in each case on the weight of the composition.

Further particularly preferred agents according to the present invention are characterized by including at least one compound that is an inhibitor of the enzyme cystathionine beta-lyase. Deodorant active agents preferred according to the present invention that act as an inhibitor of cystathionine beta-lyase are selected from those disclosed in EP 495918 B1, WO 2006/079934, DE 102010000746 A1, WO 2010/031657 A1, and WO 2010/046291 A1. Further particular preferred agents according to the present invention are characterized by including at least one compound that is an inhibitor of the enzyme cystathionine beta-lyase in a total quantity from 0.001 to 10 wt %, preferably 0.01 to 5 wt %, particularly preferably 0.1 to 2.5 wt %, based in each case on the weight of the composition.

Further particularly preferred compositions according to the present invention are characterized by including at least one cationic phospholipid of formula KPL

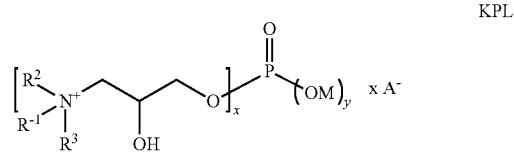

KPL in which $R^1$ is an alkyl, alkenyl, or hydroxyalkyl group having 8 to 22 carbon atoms or an acylaminoalkyl group of the formula $R^5CONH(C_mH_{2m})$—, where $R^5CO$ is a linear acyl group having 8 to 22 carbon atoms and m=2 or 3, $R^2$ and $R^3$ are alkyl groups having 1 to 4 carbon atoms or hydroxyalkyl groups having 2 to 4 carbon atoms or carboxyalkyl groups of the formula —$(CH_2)_z$—COOM, in which z has a value from 1 to 3 and M is hydrogen or an alkali metal cation, x has a value from 1 to 3 and y a value of (3-x), M is hydrogen or an alkali metal cation, and $A^-$ is an anion.

Preferred alkyl groups having 8 to 22 carbon atoms are selected from an n-octyl, n-nonyl, n-decyl, n-undecyl, lauryl, n-tridecanyl, myristyl, n-pentadecanyl, cetyl, palmityl, stearyl, elaidyl, arachidyl, behenyl, and a cocyl group. A representative cocyl group is made up, based on its total weight, of 4 to 9 wt % n-octyl groups, 4 to 9 wt % n-decyl groups, 45 to 55 wt % lauryl groups, 15 to 21 wt % myristyl groups, 8 to 13 wt % palmityl groups, and 7 to 14 wt % stearyl groups. Preferred alkenyl groups having 8 to 22 carbon atoms are selected from a linoleyl group ((9Z,12Z)-octadeca-9,12-dien-1-yl) and a linolenyl group ((9Z,12Z,15Z)-octadeca-9,12,15-trien-1-yl). A preferred hydroxyalkyl group having 8 to 22 carbon atoms is selected from a 12-hydroxystearyl group.

Particularly preferred cationic phospholipids of formula KPL are those in which $R^1$ is an acylaminoalkyl group of the formula $R^5CONH(C_mH_{2m})-$, in which $R^5CO$ represents a linear acyl group having 8 to 22 carbon atoms and m=3.

Preferred compositions according to the present invention include as a deodorizing active agent a cationic phospholipid of formula KPL

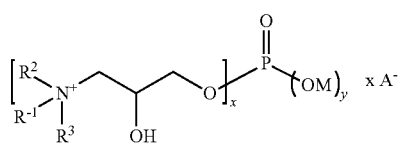

KPL in which $R^1$ is an acylaminoalkyl group of the formula $R^5CONH(C_mH_{2m})-$, in which $R^5CO$ is selected from a cocoyl group, a lauroyl group, a myristoyl group, and a linoleoyl group, and m=3, $R^2$ and $R^3$ are methyl groups, x=2, y=1, M is a sodium ion, and $A^-$ is a chloride ion. Preferably at least one cationic phospholipid of formula KPL having the features recited above is included in a total quantity from 0.05 to 2 wt %, preferably 0.1 to 1 wt %, particularly preferably 0.15 to 0.4 wt %, based in each case on the weight of the composition.

Preferred compositions according to the present invention include as a deodorizing active agent a cationic phospholipid of formula KPL

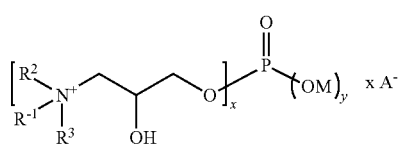

KPL in which $R^1$ is a cocoylaminopropyl group (also referred to as a cocamidopropyl group), $R^2$ and $R^3$ are methyl groups, x=2, y=1, M is a sodium ion, and $A^-$ is a chloride ion, and which is obtainable under the INCI name Cocoamidopropyl PG-Dimonium Chloride Phosphate, in a total quantity from 0.05 to 2 wt %, preferably 0.1 to 1 wt %, particularly preferably 0.15 to 0.4 wt %, based in each case on the weight of the composition.

Further particularly preferred compositions according to the present invention include as a deodorizing active agent a cationic phospholipid of formula KPL

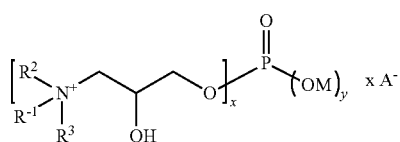

KPL in which $R^1$ is a myristoylaminopropyl group, $R^2$ and $R^3$ are methyl groups, x=2, y=1, M is a sodium ion, and $A^-$ is a chloride ion, and which is obtainable under the INCI name Myristoamidopropyl PG-Dimonium Chloride Phosphate, in a total quantity from 0.05 to 2 wt %, preferably 0.1 to 1 wt %, particularly preferably 0.15 to 0.4 wt %, based in each case on the weight of the agent.

Further particularly preferred compositions according to the present invention include as a deodorizing active agent a cationic phospholipid of formula KPL

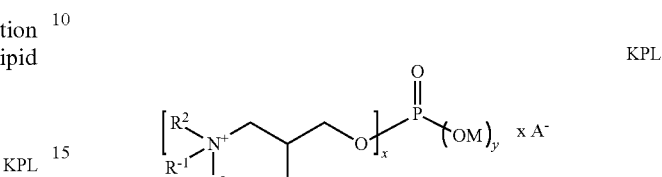

KPL in which $R^1$ is a lauroylaminopropyl group, $R^2$ and $R^3$ are methyl groups, x=2, y=1, M is a sodium ion, and $A^-$ is a chloride ion, in a total quantity from 0.05 to 2 wt %, preferably 0.1 to 1 wt %, particularly preferably 0.15 to 0.4 wt %, based in each case on the weight of the composition.

Further deodorant active agents preferred according to the present invention are odor absorbers, ion exchangers having a deodorizing effect, germ-inhibiting agents, prebiotically effective components, and enzyme inhibitors or, particularly preferably, combinations of the aforesaid active agents.

Silicates serve as odor absorbers which also, simultaneously, advantageously assist the rheological properties of the composition according to the present invention. Included among the silicates particularly preferred according to the present invention are chiefly sheet silicates, and among those in particular montmorillonite, kaolinite, illite, beidellite, nontronite, saponite, hectorite, bentonite, smectite, and talc. Further preferred odor absorbers are, for example, zeolites, zinc ricinoleate, cyclodextrins, specific metal oxides such as aluminum oxide, and chlorophyll. They are included preferably in a total quantity from 0.1 to 10 wt %, particularly preferably 0.5 to 7 wt %, and extraordinarily preferably 1 to 5 wt %, based in each case on the total composition.

"Germ-inhibiting" or "antimicrobial" active agents are understood according to the present invention as those active agents which reduce the number of skin microbes participating in odor formation, or inhibit their growth. Included among these microbes are, among others, various species from the group of Staphylococci, the group of Corynebacteria, Anaerococci, and Micrococci.

Germ-inhibiting or antimicrobial active agents preferred according to the present invention are in particular organohalogen compounds and organohalides, quaternary ammonium compounds, a number of plant extracts, and zinc compounds. These include, among others, triclosan, chlorhexidine and chlorhexidine gluconate, 3,4,4'-trichlorocarbanilide, bromochlorophen, dichlorophen, chlorothymol, chloroxylenol, hexachlorophene, dichloro-m-xylenol, dequalinium chloride, domiphen bromide, ammonium phenolsulfonate, benzalkonium halides, benzalkonium cetyl phosphate, benzalkonium saccharinate, benzethonium chloride, cetylpyridinium chloride, laurylpyridinium chloride, laurylisoquinolinium bromide, methylbenzethonium chloride. In addition, phenol, phenoxyethanol, disodiumdihydroxyethylsulfosuccinyl undecylenate, sodium bicarbonate, zinc lactate, sodium phenolsulfonate and zinc phenolsulfonate, ketoglutaric acid, terpene alcohols such as farnesol, chlorophyllin-copper complexes, as well as carboxylic acid esters of mono-, di-, and triglycerol (e.g. glycerol monolaurate, diglycerol monocaprinate) are preferred deodorant active agents.

Preferred compositions according to the present invention include at least one deodorant active agent that is selected from silver salts, aromatic alcohols of structure AA-1 having the substituents recited above, 1,2-alkanediols having 5 to 12 carbon atoms, alpha-(2-ethylhexyl)glycerol ether (3-2-ethylhexyloxy)-1,2-propanediol), tropolone, triethyl citrate, cationic phospholipids of formula KPL having the substituents recited above, as well as mixtures thereof.

Further compositions according to the present invention can include at least one vitamin or one vitamin derivative in order to improve skin compatibility. Panthenol, niacinamide, L-ascorbic acid, L-ascorbic acid esters such as ascorbyl palmitate or magnesium ascorbyl phosphate or sodium ascorbyl phosphate, 3-O-ethyl ascorbic acid, 3-O-cetyl ascorbic acid, 2-O-ethyl ascorbic acid, retinyl palmitate, tocopherol, tocopheryl acetate, and mixtures of these substances, are preferred here. Preferably at least one vitamin or one vitamin derivative is included in a total quantity from 0.01 to 2 wt %, preferably 0.1 to 1.5 wt %, particularly preferably 0.5 to 1 wt %, based in each case on the weight of the composition.

Antioxidants can likewise be included in preferred compositions according to the present invention in order to improve shelf stability and as care-providing ingredients. Preferred antioxidants are tocopherol, tocopheryl acetate, L-ascorbic acid esters such as ascorbyl palmitate or magnesium ascorbyl phosphate or sodium ascorbyl phosphate, 3-O-ethyl ascorbic acid, 3-O-cetyl ascorbic acid, 2-O-ethyl ascorbic acid lipochroman-6, and mixtures of these substances. Preferably at least one antioxidant is included in a total quantity from 0.001 to 1 wt %, preferably 0.01 to 0.6 wt %, particularly preferably 0.1 to 0.3 wt %, based in each case on the weight of the composition.

Preferred compositions according to the present invention include at least one pyridinecarboxylic acid, preferably 2,6-pyridinecarboxylic acid as protection from textile discolorations that could be caused by the compositions according to the present invention, particularly preferably in a quantity from 0.01 to 1 wt %, preferably 0.02 to 0.8 wt %, particularly preferably 0.05 to 0.6 wt %, even more preferably 0.1 to 0.4 wt %, and in particular 0.2 to 0.3 wt %, the "wt %" indications referring in each case to the total weight of the composition.

In order to improve the long-term appearance of shaved armpit skin, preferred compositions according to the present invention include at least one substance that inhibits hair growth and/or one substance that lightens the hair, particularly preferably in a total quantity respectively from 0.0001 to 1 wt %, more preferably 0.001 to 0.6 wt %, extraordinarily preferably 0.02 to 0.2 wt %, based in each case on the weight, of the composition.

Further preferred compositions according to the present invention contain, as care-providing substances to improve skin compatibility, at least one protein, one amino acid, or one peptide, for example yogurt protein, particularly preferably in a total quantity from 0.0001 to 1 wt %, more preferably 0.001 to 0.6 wt %, extraordinarily preferably 0.02 to 0.2 wt %, based on the weight of the composition.

Further preferred compositions according to the present invention include at least one solid inorganic emulsion stabilizer selected from silica, hydrophobic silica, mica (the latter also to achieve an optical luster effect), and mixtures of these inorganic substances, preferably in a total quantity form 0.01 to 1 wt %, more preferably 0.05 to 0.6 wt %, extraordinarily preferably 0.1 to 0.4 wt %, based on the weight of the composition.

Further preferred compositions according to the present invention include at least one preservative.

A further subject of the present Application is a method for nontherapeutic cosmetic perspiration-inhibiting treatment of the body, in which a perspiration-inhibiting composition in the form of an oil-in-water emulsion that is not a microemulsion, including a) at least one perspiration-inhibiting aluminum salt in a total quantity from 2 to 40 wt %, preferably 8 to 35 wt %, particularly preferably 10 to 28 wt %, and extraordinarily preferably 12 to 20 wt %, wherein the "wt %" indications refer to the total weight of active substance (USP), free of water of crystallization and free of ligands, in the agent, and in addition thereto b) in a total quantity from 0.1 to 2 wt %, preferably 0.3 to 1.5 wt %, particularly preferably 0.5 to 1.1 wt %, extraordinarily preferably 0.6 to 0.8 wt %, at least one surface-active compound having an HLB value in the range from 9 to 15, selected from the partial esters of a polyglycerol that comprises 3, 4, or 5 glycerol units with a linear or branched, saturated or unsaturated carboxylic acid having 8 to 22 carbon atoms and with an organic edible acid, and in addition thereto c) in a total quantity from 0.1 to 2.0 wt %, preferably 0.3 to 1.2 wt %, particularly preferably 0.6 to 1.1 wt %, extraordinarily preferably 0.8 to 1.0 wt %, at least one N-acyl-L-glutamic acid sodium salt of formula (GLUT-1)<

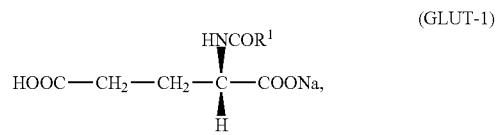

(GLUT-1)

in which $R^1CO$ represents a linear or branched, saturated or unsaturated acyl group having 6 to 22 carbon atoms, preferably having 8 to 18 carbon atoms, and in addition thereto d) at least one cosmetic oil, liquid under standard conditions, that is not a fragrance and not an essential oil, in a total quantity from 0.5 to 10 wt %, preferably 1 to 8 wt %, particularly preferably 1.5 to 6 wt %, extraordinarily preferably 2 to 4.5 wt %, and in addition thereto e) at least one hydrogel-forming polymer in a total quantity from 0.08 to 1 wt %, preferably 0.1 to 0.8 wt %, particularly preferably 0.15 to 0.6 wt %, extraordinarily preferably 0.2 to 0.4 wt %, and in addition thereto f) in a total quantity from 0.05 to 4 wt %, preferably 0.5 to 3.5 wt %, particularly preferably 1 to 3 wt %, and extraordinarily preferably 1.5 to 2.5 wt %, at least one structuring agent selected from linear saturated 1-alkanols having 14 to 22 carbon atoms, glyceryl mono- and diesters of linear or branched, saturated or unsaturated carboxylic acids having 8 to 22 carbon atoms, linear saturated 1-alkanecarboxylic acids having 14 to 22 carbon atoms, mono- and diesters of ethylene glycol with linear saturated and unsaturated fatty acids having 12 to 30, in particular 14 to 22 carbon atoms, the mono-, di-, tri-, and tetraesters of pentaerythritol with linear saturated and unsaturated fatty acids having 12 to 30, in particular 14 to 22 carbon atoms, as well as mixtures of said structuring agents,
and in addition thereto g) water in a total quantity from 30 to 90 wt %, preferably 40 to 80 wt %, particularly preferably 60 to 78 wt %, extraordinarily preferably 65 to 73 wt %, is applied onto the skin, in particular onto the skin of the armpits, wherein the "wt %" indications refer in each case to the total weight of the composition.

The statements made regarding the compositions according to the present invention apply mutatis mutandis with respect to preferred embodiments of the method according to the present invention.

A further subject of the present Application is the use of a perspiration-inhibiting composition in the form of an oil-in-water emulsion that is not a microemulsion, including a) at least one perspiration-inhibiting aluminum salt in a total quantity from 2 to 40 wt %, preferably 8 to 35 wt %, particularly preferably 10 to 28 wt %, and extraordinarily preferably 12 to 20 wt %, wherein the "wt %" indications refer to the total weight of active substance (USP), free of water of crystallization and free of ligands, in the agent,
and in addition thereto b) in a total quantity from 0.1 to 2 wt %, preferably 0.3 to 1.5 wt %, particularly preferably 0.5 to 1.1 wt %, extraordinarily preferably 0.6 to 0.8 wt %, at least one surface-active compound having an HLB value in the range from 9 to 15, selected from the partial esters of a polyglycerol that comprises 3, 4, or 5 glycerol units with a linear or branched, saturated or unsaturated carboxylic acid having 8 to 22 carbon atoms and with an organic edible acid,
and in addition thereto c) in a total quantity from 0.1 to 2.0 wt %, preferably 0.3 to 1.2 wt %, particularly preferably 0.6 to 1.1 wt %, extraordinarily preferably 0.8 to 1.0 wt %, at least one N-acyl-L-glutamic acid sodium salt of formula (GLUT-1)

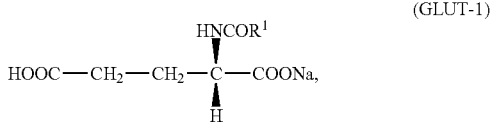

(GLUT-1)

in which $R^1CO$ represents a linear or branched, saturated or unsaturated acyl group having 6 to 22 carbon atoms, preferably having 8 to 18 carbon atoms,
and in addition thereto d) at least one cosmetic oil, liquid under standard conditions, that is not a fragrance and not an essential oil, in a total quantity from 0.5 to 10 wt %, preferably 1 to 8 wt %, particularly preferably 1.5 to 6 wt %, extraordinarily preferably 2 to 4.5 wt %,
and in addition thereto e) at least one hydrogel-forming polymer in a total quantity from 0.08 to 1 wt %, preferably 0.1 to 0.8 wt %, particularly preferably 0.15 to 0.6 wt %, extraordinarily preferably 0.2 to 0.4 wt %,
and in addition thereto f) in a total quantity from 0.05 to 4 wt %, preferably 0.5 to 3.5 wt %, particularly preferably 1 to 3 wt %, and extraordinarily preferably 1.5 to 2.5 wt %, at least one structuring agent selected from linear saturated 1-alkanols having 14 to 22 carbon atoms, glyceryl mono- and diesters of linear or branched, saturated or unsaturated carboxylic acids having 8 to 22 carbon atoms, linear saturated 1-alkanecarboxylic acids having 14 to 22 carbon atoms, mono- and diesters of ethylene glycol with linear saturated and unsaturated fatty acids having 12 to 30, in particular 14 to 22 carbon atoms, the mono-, di-, tri-, and tetraesters of pentaerythritol with linear saturated and unsaturated fatty acids having 12 to 30, in particular 14 to 22 carbon atoms, as well as mixtures of said structuring agents,
and in addition thereto g) water in a total quantity from 30 to 90 wt %, preferably 40 to 80 wt %, particularly preferably 60 to 78 wt %, extraordinarily preferably 65 to 73 wt %, for nontherapeutic cosmetic perspiration-inhibiting treatment of the body, wherein the "wt %" indications refer in each case to the total weight of the composition.

The statements made regarding the compositions according to the present invention apply mutatis mutandis with respect to preferred embodiments of the use according to the present invention.

The examples below are intended to illustrate the subject matter of the present invention without, however, limiting it thereto (all indications in wt %).

Antiperspirant roll-ons in the form of an oil-in-water emulsion (not microemulsions)

| Commercial name | INCI | No. 1 | No. 2 | No. 3 |
|---|---|---|---|---|
| Eumulgin SG | Sodium Stearoyl Glutamate | 0.6 | 0.6 | 0.8 |
| Lanette 18 | Stearyl Alcohol | 2.5 | 1.5 | 1.5 |
| Myritol 318 | Caprylic/Capric Triglyceride | 2.5 | 2.5 | 2 |
| Tego Care PSC 3 | Polyglyceryl-3 Dicitrate/Stearate | 0.8 | 0.8 | 0.6 |
| Tylose H 100000 YP2 | Hydroxyethylcellulose | 0.25 | 0.25 | 0.25 |
| Aluminum chlorohydrate 50% naS | Aluminum Chlorohydrate | 40 | 20 | 10 |
| 1,2-Propanediol | Propylene Glycol | 5 | 5 | 5 |
| Perfume | Parfum | 1 | 1 | 1 |
| Water (deionized) | Aqua (Water) | 47.35 | 68.35 | 78.85 |

| Commercial name | INCI | No. 4 | No. 5 | No. 6 |
|---|---|---|---|---|
| Eumulgin SG | Sodium Stearoyl Glutamate | 0.95 | 1 | 0.4 |
| Lanette 18 | Stearyl Alcohol | 1.5 | 1.5 | 1.5 |
| Myritol 318 | Caprylic/Capric Triglyceride | 2.8 | 2.5 | 2.5 |
| Tego Care PSC 3 | Polyglyceryl-3 Dicitrate/Stearate | 0.5 | 0.4 | 1 |
| Tylose H 100000 YP2 | Hydroxyethylcellulose | 0.3 | 0.25 | 0.3 |
| Aluminum chlorohydrate 50% naS | Aluminum Chlorohydrate | 20 | 10 | 10 |
| 1,2-Propanediol | Propylene Glycol | 5 | 5 | 5 |
| Perfume | Parfum | 1 | 1 | 1 |
| Water (deionized) | Aqua (Water) | 67.9 | 78.35 | 78.3 |

Aluminum chlorohydrate 50% naS: 50-wt % aqueous solution of non-activated aluminum chlorohydrate.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A perspiration inhibiting composition in the form of an oil-in-water emulsion that is not a microemulsion, comprising
   a) 2 to 40 wt % perspiration-inhibiting aluminum salt,
   b) 0.1 to 2 wt % Polyglyceryl-3 Dicitrate/Stearate,
   c) 0.1 to 2.0 wt % N-stearoylsodium-L-glutamate,
   d) 0.5 to 10 wt % cosmetic oil,
   e) 0.08 to 1 wt % hydroxyethyl cellulose,
   f) 0.05 to 4 wt % stearyl alcohol, and
   g) 30 to 90 wt % water.

2. The composition according to claim 1, including
   a) 8 to 35 wt % perspiration-inhibiting aluminum salt,
   b) 0.3 to 1.5 wt % Polyglyceryl-3 Dicitrate/Stearate,
   c) 0.3 to 1.2 wt % N-stearoylsodium-L-glutamate,
   d) 1 to 8 wt % cosmetic oil,
   e) 0.1 to 0.8 wt % hydroxyethyl cellulose,
   f) 0.5 to 3.5 wt % stearyl alcohol, and
   g) 40 to 80 wt % water.

3. The composition according to claim 1, including
   a) 10 to 28 wt % perspiration-inhibiting aluminum salt,
   b) 0.5 to 1.1 wt % Polyglyceryl-3 Dicitrate/Stearate,
   c) 0.6 to 1.1 wt % N-stearoylsodium-L-glutamate,
   d) 1.5 to 6 wt % cosmetic oil,
   e) 0.15 to 0.6 wt % hydroxyethyl cellulose,
   f) 1 to 3 wt % stearyl alcohol, and
   g) 60 to 78 wt % water.

4. The composition according to claim 1, including
   a) 12 to 20 wt % perspiration-inhibiting aluminum salt,
   b) 0.6 to 0.8 wt % Polyglyceryl-3 Dicitrate/Stearate,
   c) 0.8 to 1.0 wt % N-stearoylsodium-L-glutamate,
   d) 2 to 4.5 wt % cosmetic oil,
   e) 0.2 to 0.4 wt % hydroxyethyl cellulose,
   f) 1.5 to 2.5 wt % stearyl alcohol, and
   g) 65 to 73 wt % water.

* * * * *